(12) United States Patent
Rubio et al.

(10) Patent No.: US 7,014,875 B2
(45) Date of Patent: *Mar. 21, 2006

(54) CONTINUOUS ENZYMATIC PRECOOKING FOR THE PRODUCTION OF AN INSTANT CORN FLOUR FOR SNACK AND TORTILLA

(75) Inventors: Manuel J. Rubio, Miami Beach, FL (US); Roberto Contreras, Guadalupe, N.L. (MX); Felipe A. Rubio, Edinburg, TX (US); Juan Fernando Ramirez, Guadalupe N.L. (MX)

(73) Assignee: Roberto Gonzalez BARRERA, Guadalupe (MX)

( * ) Notice: Subject to any disclaimer, the term of this patent is extended or adjusted under 35 U.S.C. 154(b) by 134 days.

This patent is subject to a terminal disclaimer.

(21) Appl. No.: 10/653,361

(22) Filed: Aug. 28, 2003

(65) Prior Publication Data

US 2004/0105925 A1   Jun. 3, 2004

Related U.S. Application Data

(63) Continuation-in-part of application No. 10/231,291, filed on Aug. 30, 2002, now Pat. No. 6,638,554.

(51) Int. Cl.
 *A23L 1/00* (2006.01)
(52) U.S. Cl. .................. 426/52; 426/507; 426/509; 426/463; 426/622
(58) Field of Classification Search ................ 426/507, 426/509, 463, 464, 481, 518, 622, 626, 18, 426/52
See application file for complete search history.

(56) References Cited

U.S. PATENT DOCUMENTS 2,584,893 A  2/1952 Lloyd 2,704,257 A  3/1955 De Sollano et al.
3,194,664 A  7/1965 Eytinge (Continued)

FOREIGN PATENT DOCUMENTS

CA   2015149   10/1990

(Continued)

OTHER PUBLICATIONS

Mario M. Alvarez et al., Biodegradative Treatment of Nixtamalization Wastewaters (Nejayote), Using Immobilized Native Mixed Culture in Anoxic Environments, Abstract in Keystone Symposia of Environmental Biotechnology, Journal of Cellular Biochemistry, 1995, one page.

(Continued)

*Primary Examiner*—Drew Becker
(74) *Attorney, Agent, or Firm*—Young & Thompson

(57) ABSTRACT

Precooked and partially debranned corn flour is continuously produced by an enzymatic precooking using a commercial endoxylanase and endoamylase blend as a processing aid. The low-temperature and near neutral-pH precooking with an endoxylanase and endoamylase solution effects a partial hydrolysis of bran and starchy cell-walls with a controlled gelatinization and reduced conditioning and corn solid loss in wastewater. Moisture content is then stabilized after washing, followed by milling and drying at a high temperature for a short time to produce a partial gelatinization in the ground kernel, cooling and further drying the dried-milled particle. A fine particle size or flour is separated and recovered from the coarser particle which is also segregated to isolate a light bran fraction for integral flour or feed use, remilling and sieving the coarser particle to produce an instant corn flour for snack chip and corn-based food, and admixing the fine particle with lime to obtain a masa flour for tortillas and the like.

14 Claims, 1 Drawing Sheet

U.S. PATENT DOCUMENTS

| | | | |
|---|---|---|---|
| 3,730,732 | A | 5/1973 | Rubio |
| 4,513,018 | A | 4/1985 | Rubio |
| 4,594,260 | A | 6/1986 | Vaqueiro et al. |
| 4,990,343 | A | 2/1991 | Haarasilta et al. |
| 5,176,931 | A | 1/1993 | Herbster |
| 5,447,742 | A | 9/1995 | Malvido et al. |
| 5,532,013 | A | 7/1996 | Martinez-Bustos et al. |
| 5,558,898 | A | 9/1996 | Sunderland |
| 5,662,901 | A | 9/1997 | Tobey, Jr. et al. |
| 5,698,245 | A | 12/1997 | Tanaka et al. |
| 6,025,011 | A | 2/2000 | Wilkinson et al. |
| 6,066,356 | A | 5/2000 | Van Der Wouw et al. |
| 6,068,873 | A | 5/2000 | Delrue et al. |
| 6,265,013 | B1 | 7/2001 | Martinez-Montes et al. |
| 6,322,836 | B1 | 11/2001 | Rubio et al. |
| 6,326,045 | B1 | 12/2001 | Rubio et al. |
| 6,344,228 | B1 | 2/2002 | Rubio et al. |
| 6,387,437 | B1 | 5/2002 | Martinez-Bustos et al. |
| 6,428,828 | B1 | 8/2002 | Jackson et al. |
| 6,516,710 | B1 | 2/2003 | Knight et al. |

FOREIGN PATENT DOCUMENTS

| | | |
|---|---|---|
| EP | 0 338 787 A2 | 10/1989 |
| GB | 2 371 205 A | 7/2002 |
| MX | 9502200 | 1/1997 |
| WO | 00/45647 | 8/2000 |
| WO | 01/98509 A2 | 12/2001 |

OTHER PUBLICATIONS

Cory M. Bryant et al., "Effect of Lime on Gelatinization of Corn Flour and Starch," Cereal Chem., V. 74, 1997, pp. 171, 173-175.

Enzyme Technical Association, Enzymes Used in Food Processing (as compiled by the ETA Member), (www.enzymetechnicalassoc.org), pp. 1-7.

Food and Drug Administration, CFSCAN-Office of premarket approval: Partial list of enzyme preparations that are used in foods/Summary-GRAS notices (www.cfsan.fda.gov), pp. 1-4.

Z. Hromadkova et al., "Isolation and Characterizaton of Hemicelluloses of Corn Hulls," Chem. Papers, V. 49, 1995, pp. 97-100.

INCAP, Food Composition Table for use in Latin America, By: Leung, W.W. et al, INCAP and NIH-project, Guatemala City, Guatemala, C.A. 1961, pp. 12-15.

Thomas W. Jeffries, "Biochemistry and Genetics of Microbial Xylanases," Current Opinion in Biotechnology, V. 7, 1996, pp. 337-342.

Ricardo Martinez et al., "Kinetic Approach to Nixtamalization of Corn Pericarp," Cereal Chem., V. 78, 2001, pp. 107-110.

P.R. Mathewson, Enzymes, An Eagan Press Handbook Series, 1998, pp. 15-19, 25-34, 91, and 93-95.

E. Montemayor et al., Alkaline Cooked Flour: Technology and use in tortilla and snack products, Cereal Foods World, V. 28, 1983, Abstract.

J.F. Ramirez et al., "Microbial Interactions in the Mexican Pozol Fermentation," Proceedings in the Ecology of Fermented Foods, IV-International Symposium in Microbial Ecology, Ljubljana, Yugoslavia, 1986, pp. 299-301.

D. Sahai et al., "A Novel Enzymatic Nixtamalization Process for Producing Corn Masa Flour," Cereal Foods World, V. 46, 2001, pp. 240-245.

Luc Saulnier et al., "Cell Wall Polysaccharide Interactions in Maize Bran," Carbohydrate Polymers, V. 26, 1995, pp. 279, 281, 284-286.

Keith H. Steinkraus, "Indigenous Fermented Foods Involving an Alkaline Fermentation," Handbook of Indigenous Fermented Foods, 2nd ed., 1996, pp. 349-350, 357-360.

Ricardo Bressani et al., SUSTAIN, Fortification of Corn Masa Flour with Iron and/or Other Nutrients—A Literature and Industry Experience Review, 1997, pp. 34, 37-38, 46, 49, 61, 74-78, and 136.

Stanley A. Watson, "Chapter 3: Structure and Composition," Corn Chemistry and Technology, ed. by S.A. Watson et al., AACC, 1987, pp. 53-82.

N. Yao et al, "Thermal Properties of Floury and Horny Corn Endosperm," Pennsylvania State Department of Food Science, Pennsylvania State University, one page.

Tortillas, ready-t-bake or -fry, corn, www.nal.usda.gov/fnic/cgi-bin/list mut.pl, NDB No.: 18363, 3 pages.

CONTINUOUS ENZYMATIC PRECOOKING FOR THE PRODUCTION OF AN INSTANT CORN FLOUR FOR SNACK AND TORTILLA

This is a Continuation-in-part of application Ser. No. 10/231,291 filed Aug. 30, 2002.

BACKGROUND OF INVENTION

1. Field of the Invention

The present invention relates to a method of low-temperature and near neutral-pH precooking for the production of corn flour and, more particularly, to one that achieves continuous partial hydrolysis of the bran heteroxylans and starchy cell-walls and avoids excessive pregelatinization with an endoxylanase and endoamylase blend as a processing aid during the manufacture of an instant corn flour for snack and tortilla making.

2. Description of Related Art he production of high-quality masa flour can be produced by conventional techniques only if the food-grade dent corn has the following characteristics: uniformity in kernel size and hardness, low number of stress-cracks and kernel damage and ease of pericarp removal during the lime-water cooking process. The mature kernel has four separable components, on a dry weight basis: tip cap (0.8–1.1%), pericarp or bran (5.1–5.7%), endosperm (81.1–83.5%), and germ (10.2–11.9%). Although bran is sometimes used as a synonym for pericarp, in the dry or wet-milling processes the bran includes the pericarp, tip cap, aleurone layer (isolated with bran) and adhering pieces of starchy endosperm as well. A native corn bran contained some starch (4–22%) and proteins (5–8%) arising from endosperm tissue (Saulnier et al. 1995 and Hromadkova et al. 1995). Nixtamalized corn flour (NCF) is produced by the steps of alkaline cooking of corn, washing, milling the nixtamal and drying to give corn masa flour. This flour is sieved and blended for different product applications and it is usually supplemented with additives before packaging for commercial table or packaged-tortilla and snack production. Although the pericarp is partially removed during the alkaline-cooking and washing process stages, there is still fiber left from the corn kernel from either a continuous or batch process (Montemayor and Rubio, 1983, U.S. Pat. No. 4,513,018). Nixtamalized corn flour or Industrial masa flour can contain from 7–9% of total dietary fiber or bran with 6–8% mainly consisting of insoluble fiber on a dry basis (Sustain, 1997).

The cell walls or non-starch polysaccharides (NSP) are the major corn dietary fiber components and are composed of hemicellulose (heteroxylan or pentosan and β-glucan: 4.4–6.2%), cellulose (2.5–3.3%) and some lignin (0.2%). According to Watson (1987: Tables IV and VII), the corn pericarp/tip cap makes up about 5–6% and aleurone-endosperm has about 2% of the kernel dry weight . This pericarp also contains 90% insoluble fiber (67% hemicellulose and 23% cellulose) and only 0.6% soluble-fiber (soluble-arabinoxylan and β-glucan). It is estimated that dietary fiber in both pericarp (4.9%) and endosperm (2.6%) make up 80% of the total dietary fiber. The corn insoluble fiber is mainly found in the pericarp and endosperm (aleurone and starchy), which make up 68% of the total dietary fiber (9.5% in a dry-weight basis). All corn bran layers comprise the outer (beeswing or hull), inner (cross and tube cells), nucellar layer and endosperm (aleurone and starchy) cell-walls. The innermost tube-cell layer is a row of longitudinal tubes pressed tightly against the aleurone layer. Next there is a very loose and open area called the cross-cell layer, which has a great deal of intercellular space. These areas provide capillary interconnections between all cells, which facilitate water absorption. The pericarp extends to the base of the kernel, uniting with the tip cap. Inside the tip cap there are spongy-branched cells openly connected with the cross-cells.

Unlike corn endosperm, in which soluble fiber amounts to 12% of the total fiber (4.1%), in whole wheat, soluble fiber represents 22% of total fiber (about 20% of the flour water-uptake is bound to the soluble pentosan fraction). Arabinoxylan is a complex polymer (20,000–170,000 Daltons) with a linear backbone of (1,4)-β-xylopiranosyl units to which substituents are attached through O2 and O3 atoms of the xylosil residues (mainly, α-L-arabinofuranosyl). This polymer is apparently linked to the cellulose skeleton in the corn cell wall by ester linkage cross-bonding through ferulic and diferulic acid (Watson, 1987). However, heteroxylan insolubility in corn bran might be due to protein-polysaccharide linkages and a highly branched structure (23% of the xylan backbone does not bear side-chains) as opposed to wheat bran (Saulnier et al., 1995).

During alkali-cooking and/or steeping, there are chemical and physical changes such as nutrient losses along with partial pericarp or bran removal, degradation of the endosperm periphery with starch gelatinization/swelling and protein denaturation in the precooked corn kernel. The most important nutritional modifications are: an increase in the calcium level with improvement in the Ca to P ratio, a decrease in insoluble dietary fiber and zein-protein, a reduction in thiamin and riboflavin, an improvement of the leucine to isoleucine ratio reducing the requirement for niacin, a niacin availability by hydrolysis of hemicellulosic aleurone and germ fractions, and leaching the aflatoxins into the wastewater (Sustain, 1997). The known cooking methods (batch/continuous) have been proposed as the critical variables (Sahai et al., 2001 and U.S. Pat. No. 6,516,710) which determine soluble-solids loss in limewater residue for anaerobic biodegradation (1% to 1.6% COD; Alvarez and Ramirez, 1995). Dry solid matter (1.5%–2.5%) includes an average of 50–60% dietary fiber (with 12–13% crude fiber), 15–20% ash, 15% starch, 5–10% protein and 5% fat. Bryant et al., (1997) showed an optimum change in starch behavior at a lime level similar to the corn masa industry where starch gelatinization indicators (enzyme digestion, water retention capacity, starch solubility and DSC-peak temperature=69° to 75° C.) are increased with lime addition of 0 to 0.4%, peaking at 0.2%. They also found a peak-viscosity temperature reduction upon the addition of lime up to 0.5%, indicating faster granule swelling that requires less thermal energy. Corn pericarp nixtamalization (Martinez et al., 2001) has a first-order stage associated with a fast dissolution of hot-water soluble fractions as starch and pectin, and alkali-soluble fat. A second stage is due to a slow alkaline-hydrolysis of the hemicellulose-cellulose-lignin structure with a higher hemicellulose loss proportional to alkaline-pH concentrations.

Arabinoxylan degrading enzymes include xylanases (1,4-β-D-xylan xylanohydrolase, EC 3.2.1.8) and β-xylosidases (1,4-β-D-xylan xylohydrolase, EC 3.2.1.37). The former enzyme randomly hydrolyzes the insoluble and soluble xylan backbone (EC 3.2.1.8) whereas the latter enzyme hydrolyzes xylose from the non-reducing end of the xylose-polymer (EC 3.2.1.37). Xylose is not usually the major product and it is typically produced after xylobiose and xylotriose (smallest oligomer). Virtually all xylanases are endo-acting as determined by chromatography or their kinetic properties (substrate and product formation), molecular weight and pH (basic or acidic) or its DNA sequence (crystal structure). They can be structurally classified into two major families or isoenzymes (F or 10 and G or 11) of glycosyl hydrolases (Jeffries, 1996). F10 xylanases are larger, with some cellulase activity and produce low DP oligosaccharides (less specific); G11 are more specific for xylan and with lower molecular weight (e.g., *Bacillus circulans* and *Trichoderma harzianum*).

In addition, the Enzyme Technical Association (ETA, 1999; FDA, 1998) classified as carbohydrases the following hemicellulases (trivial name): a) endoenzymes split anywhere along the polymer chain (EC 3.2.1.8, EC 3.2.1.32=1, 3-β-xylanohydrolase, 78=mannanohydrolase and 99=arabinohydrolase) and b) exoenzymes only attack branches or terminal bonds on the xylose-polymer, producing xylo-oligomers (EC 3.2.1.37, EC 3.2.1.55=αL-arabinofuranosyl, glucuronic-acid glycosilase and ferulic-acid esterase). Currently recognized endoenzymes (xylanases) and exoenzymes produced from *A. niger* (EC 3.2.1.8 and 37,55), *A. oryzae* (EC 3.2.1.8 or 32), *B.subtilis* (EC 3.2.1.99), and *Trichoderma longibrachiatum* (formerly *reesei*: EC 3.2.1.8) are Generally Recognized As Safe (GRAS; 21 CFR 182, 184 and 186) and require no further approval from the U.S. Food and Drug Administration or Recognized As Safe (RAS in Europe: Mathewson, 1998). However, direct and indirect food additives (i.e., packaging materials) are regulated in 21 CFR 172 and 174–178 as well. Secondary direct additives, a sub-class of direct additives, are primarily Processing Aids which are used to accomplish a technical effect during food processing but are not intended to serve a technical or as a functional additive in the finished food. They are also regulated in 21 CFR 173 (Partial List of Enzyme Preparations that are used in foods). Finally, all GRAS Substances made with recombinant-DNA technology which were widely consumed prior to 1958, and which have been modified and commercially introduced after 1958 must comply with regulatory requirements proposed in 21 CFR 170.3 (GRAS Notice).

The benefits of using a commercial xylanase (endoenzyme) in cereal flours instead of a non-specific hemicellulase (endo/exoenzyme) preparation are a reduction in side activities (cellulase, beta-glucanase, protease and amylase) and a reduction of dough-stickininess. Arabinoxylan degrading enzymes with well defined endo-acting and exo-acting activities have become commercially available, for food and feed, from the following companies: Alltech, Amano, Danisco-Cultor, EDC/EB, Genencor, Gist-Brocades, Iogen, Novo, Primalco, Rhodia and Rohm. Suggested applications for commercial xylanases (endopentosanases) and hemicellulases (endo/exopentosanases) mentioned in the literature include: 1) improving the watering of spent grains and energy reduction during drying; 2) facilitation of dough formulation with less water, reduction of stickiness in noodle and pasta production; 3) reduction in the water content when formulating grains for flaking, puffing or extrusion; 4) retarding staling or hardening in bread; 5) relaxing dough for cookie and cracker production and use of sticky cereal flours in new products; 6) increase in bran removal when added to tempering water; 7) reducing both steeping time and starchy fiber in corn wet milling; and 8) an exo-acting xylanase can enhance reducing-sugars and amino acids reactions.

A complex set of conditions determines bakery product shelf life, so the food formulator has three basic approaches to crumb softness: prevent moisture transfer; prevent starch recrystallization; and hydrolyze starch. Crumb staling is marked by many physicochemical changes which occur in the following order: hardening and toughening of the crumb (starch retrogradation); appearance of crumbliness; and moisture loss by evaporation. Commercial amylases act as anti-staling agents by breaking down gelatinized starch during baking. Some commercial microbial amylases (ETA, 1999;FDA, 1998) are listed by name and source are: a) endo-amylase (*A. oryzae/niger*, and *R. oryzae/niveus*: EC 3.2.1.1); b) exo-glucoamylase/exo-amyloglucosidase (*R. oryzae/niveus* and *Aspergillus oryzae/niger*: EC 3.2.1.3); and c) endo-pullulanase and endo-amylase (*B. subtilis, B. megaterium, B. stearohtermophilus* and *Bacillus* spp.: EC 3.2.1.33,41/68 and EC 3.2,1,133). Genetic engineering technology has been used to develop amylases with endo or exo-acting (maltogenic) activity with intermediate thermo-stability (<65° C.) and *B. stearothermophilus* falls into this category. These novel amylases are fully inactivated during baking while yielding a soft crumb without gumminess even at higher dosages. Lopez-Mungia et al. (MX Patent 952,200) described an enzymatic process (with endo-amylases) to obtain corn tortillas (from nixtamal or nixtamalized corn flour), which delays staling during ambient or frozen storage.

A moderate exoxylanase addition decreases water uptake in wheat dough, whereas using an endoxylanase increases water binding and soluble-xylans as well for a high-moisture bread product. On the contrary, if starch gelatinization is to be minimized, a higher endozyme addition is desirable and hydrolysis of the soluble fraction releases water for low-moisture cookie or cracker products (EPA Patent 0/338787). Therefore, a suitable level of endoxylanase results in desirable dough softening without causing stickiness, thereby improving machinability during forming and baking operations. Haarasilta et al. (U.S. Pat. No. 4,990,343) and Tanaka et al. (U.S. Pat. No. 5,698,245) have proposed that a preparation of hemicellulase or pentosanase with a cellulase (Cultor/Amano) causes decomposition of wheat insoluble fiber for bread volume increase. Rubio et al. (UK Patent 2,371,205) improved the flexibility and elasticity of packaged corn tortillas after 7 days of ambient storage by adding a fungal enzyme mixture of hemicellulase and cellulase (>100 ppm) to the nixtamalized corn flour.

Antrim et al. (CA Patent 2,015,149) disclosed a process of preparing a shredded, farinaceous product by cooking whole grain (wheat), treating it with a microbial isoamylase, tempering (i.e., holding) and forming in order to bake or toast the shredded wheat product. Tobey et al. (U.S. Pat. No. 5,662,901) have used an enzyme formula (>200 ppm) and conditioned the wet or soaked grain (sorghum) for at least 30 minutes. The microbial enzymes comprised a hemicellulase, an amylase, a pectinase, a cellulase and a protease to increase both animal weight gain and feed use efficiency. Van Der Wouw et al. (U.S. Pat. No. 6,066,356) also reported the use of a recombinant-DNA endo-arabinoxylanase (Gist Brocades) breaks down the water-insoluble-solids (~1.5%) from degermed maize and increases their in-vitro digestion (13%–19%) for animal feed or in wheat flour for improving its bread volume (~9%).

A pilot process (WO Patent 00/45647) for the preparation of a modified masa foodstuff used a reducing agent (metabisulfite) or an enzyme as a processing aid (disulfide isomerase or acid thiol-protease/Danisco) with masa or whole corn prior to a batch nixtamalization such that the native protein is modified. Jackson et al. (U.S. Pat. No. 6,428,828) disclosed a similar batch process where whole-kernel was steeped and digested with a commercial alkaline-protease (<500–1000 ppm at 50°–60° C.; pH >9 with >450 ppm lime), which altered zein structure similarly to alkali-cooking with a partial gelatinization (~20–40%).

A novel transgenic thermostable-thioredoxin enzyme was cloned in corn (high-protein) mainly to enhance extractability and recovery of starch and protein important in flaking grit and in masa production. Reduction of protein disulphide bonds alters the nature of corn flour (as a wheat flour substitute from high-protein corn varieties) during steeping or conditioning of the kernel from 45° C. to 95° C. instead of using sulfites. The batch steeping is required to soften the kernel and then to loosen starch granules from the complicated matrix of proteins and cell wall material that makes up the corn endosperm (WO. Patent 01/98509).

Tortilla is the main edible corn product in North and Central America. It is a flat, round, unleavened and baked thin pancake (flat-cornbread) made from fresh masa or corn dough prepared from industrial nixtamalized corn flour (lime-treated corn flour). It might be mentioned that tortilla, when manually or mechanically elaborated and without additives of any kind, has a maximum shelf life of 12 hours at room temperature (U.S. Pat. No. 3,730,732). Afterwards they are spoiled by contaminating microorganisms (ropy-bacteria: *Bacillus* spp. or moldy-spots) and become hard or stale (starch retrogradation) due to microbial/physicochemical changes in the starch constituent of either stored or reheated tortilla. It is known that tortillas when kept under conditions in which no moisture is lost, nevertheless become inflexible with time and break or crumble easily when bent. In northern South America, particularly in Colombia and Venezuela, hard endosperm corn is processed with dry milling technology without wastewater and it is further converted into a precooked, degermed and debranned flour for traditional corn foods. Its consumption is mainly in the form of "arepa", which is a flat or ovoid-shaped, unleavened, and baked thick pancake made from instant corn flour. In other South American countries, corn meal (coarse grind) and corn flour (fine grind) are used for different bakery (e.g., corn bread, pancake), batters and snacks.

Food fermentation processes are reliant on both endogenous and microbial enzymatic activities for the degradation of fibers, starches, proteins, anti-nutritional and toxic factors. In some cases, microbial processes are associated with indigenous fermentation processes, which exhibit unique properties. Microorganisms are currently the primary source of industrial enzymes: 50% are derived from fungi and yeast; 35% from bacteria, while the remaining 15% are either of plant or animal origin. Microbial enzymes are commercially produced either through submerged fermentation or solid-substrate fermentation technologies. The use of biocatalysts or enzymes has the potential to increase productivity, efficiency and quality output in agro-industrial processing operations in many emerging countries. These biochemical processes generally have requirements for a simple manufacturing base, low capital investment and lower energy consumption than other food processing unit operations. Alkaline and neutral-pH fermentations of various beans (soy and locust), seeds, and leaves provide protein/lipid rich, flavorsome, low-cost food condiments to millions of people mainly in Africa and Asia (Nigerian dawadawa/ogiri, Sierra Leone ogiri-saro, Japanese natto, Indian kenima, Indonesian cabuk/semayi). Based upon the use of *Bacillus* spp. (*B. subtilis B. licheniformis, B. pumilus*), the fermentations are primarily proteolytic, yielding amino acid/peptide-rich mixtures without microbial amylase and lipase activities in food substrates (Steinkraus, 1996). Pozol is a fermented corn doughball (from nixtamal or lime-treated maize) produced and consumed, as a beverage/porridge, by the indigenous and mestizo population in S.E. Mexico. It is a complex 10-days lactic fermentation involving at least five interacting groups. These include the natural flora in the freshly prepared dough or nixtamalized corn flour (heat-resistant *Bacillus* spp. and *Actinomycetes* spp.); *A. azotophilum* and *K. pneumonia* (*E. aerogenes*), both of which grow in nitrogen-free media and are likely to increase the crude microbial protein during this solid-substrate fermentation. The other groups include a lactic-acid bacterium (amylolytic *Lactobacillus* sp.), which increases its flavor (0.7% lactic-acid) while lowering the alkaline pH (from 8 to ~5); *C. tropicalis* which contributes to aroma (fruity), and *G. candidum* which produces a spongy texture (Ramirez and Steinkraus, 1986). On the other hand, a corn wet-milling process for starch production involves an acid (pH <5) fermentation during steeping or soaking whole corn kernels counter-currently (24–48 hours at 45–50° C.). The purpose is to soften the endosperm and to break the disulfide-bonds holding the protein matrix together. Steeping is a diffusion limited unit operation where two steep-water chemical and biochemical aids are required (with ~0.10–0.25% sulfur dioxide and ~0.5–2.0% lactic-acid usually produced by *Lactobacillus* spp.). They can diffuse into the corn kernel through the base end of the tip cap, move through the cross and tube cells of the pericarp to the kernel crown and into the endosperm (Watson, 1987). The main result of a lactic fermentation is a dispersion of endosperm protein/zein and an enhancement of starch release during subsequent milling for acid-fermented corn gruels/porridges such as: Ghanian kenkey, Nigerian ogi (industrial), Kenyan uji and South African mahewu (Steinkraus, 1996).

Properly processed industrial corn or masa flour simplifies the production of tortilla and snack products, because the customer eliminates management techniques required for wastewater treatment, securing, handling and processing corn into fresh masa for tortillas and snacks. However, an instant corn flour might have the following quality and cost disadvantages: high cost, lack of flavor and poor texture in masa and third-generation (3G) corn foods. These may include extrusion cooking, followed by cooling, holding (aging) and drying to make "snack pellets" which are expanded by frying to make the final snack product. Another example is breakfast cereals made by cooking whole grain (wheat, rice, or corn), followed by cooling, tempering (conditioning), shredding, forming into "biscuits" and baking.

Corn processors can generate added value from their industrial operations in one of three approaches: developing new products from new hybrids, increasing the yield of traditional products from corn, and improving process efficiency at a lower unit cost. In the past, this has been done by methods and using an apparatus in which the grain is cooked and/or steeped in a lime-water solution such as those disclosed in U.S. Pat. Nos. 2,584,893, 2,704,257, 3,194,664, and 4,513,018. These prior art methods for the industrial production of corn dough or masa flour involve accelerated cooking and steeping times with large amounts of solids losses (~1.5–2.5%) in the liquid waste. In addition, micro-nutrients such as vitamins and minerals are lost, depending on the severity of the cook and wash stages.

Many and varied methods for the production of instant corn flour for food products involving reduced amounts of water with low-temperature cooking and short-time processing for a high yield of the end product have been developed, as reflected by the following U.S. Pat. Nos. 4,594,260, 5,176,931, 5,532,013, and 6,387,437. In this connection, reference is made to the following U.S. Pat. Nos. 4,594,260, 5,176,931, 5,532,013, and 6,265,013 also requiring a low-temperature drying. On the contrary, U.S. Pat. Nos. 4,513,018, 5,447,742 5,558,898, 6,068,873, 6,322,836, 6,344,228 and 6,516,710 used a high-temperature dehydration or cooking in place of a low-temperature cooking.

Having in mind the disadvantages of the prior art methods, several studies not only have used a low-temperature precooking with minimum wastewater, but also separate corn fractions as reflected by the following U.S. Pat. Nos. 4,594,260, 5,532,013, 6,025,011, 6,068,873, 6,265,013, 6,326,045 and 6,516,710.

A few applications for enzymatic steeping were also tested to convert a traditional masa processing with reduced wastewater into a novel biochemical process (WO Patent 00/45647 and U.S. Pat. No. 6,428,828) Although the above described prior art methods are capable of an acid or an alkaline-enzymatic precooking or steeping of the whole corn for either modified masa or masa flour processing, a continuous industrial application using instead an endoxylanase and endoamylase as a processing aid, at near neutral-pH, was still unavailable in the market at the time of the invention.

SUMMARY AND OBJECTS OF THE INVENTION

Accordingly, it is an object of this invention to provide a complete departure from the prior art accelerated precooking methods of thermal, mechanical, chemical and enzymatic or biocatalytical processing of whole corn in order to control starchy endosperm gelatinization without using chemical aids during production of an instant corn flour for snacks and tortillas.

It is another object of this invention to use low-temperature cooking with a microbial endoxylanase and endoamylase solution for a partial hydrolysis of corn bran heteroxylans and starchy cell-walls during the continuous production of precooked corn flour. A combined use of a commercial endoxylanase and endoamylase solution is preferred.

Another object is to use an industrial method and apparatus involving a low-temperature, near neutral-pH precooking which not only solubilizes corn cell-walls along with a slower water diffusion effecting a controlled starch granule swelling, but also results in a reduced corn solid loss.

The above and other objects and advantages of the invention are achieved by a new continuous process applied to the production of precooked corn flour or instant corn flour for snacks and tortillas, embodiments of which include a short-time corn precooking followed by a low-temperature and near neutral-pH precooking with an endoxylanase and endoamylase solution as a processing aid so as to effect a partial hydrolysis of dietary fiber and starchy cell-walls below the gelatinization temperature, reduced conditioning of precooked kernel and corn solid loss, washing and stabilization of the moisture content to a desired optimum level for grinding, milling and drying the preconditioned kernel to produce a uniform partial gelatinization, cooling and drying the dry-ground particle, separating and recovering the fine grind so produced from the coarser grind while the latter is further aspirated to remove a bran fraction for integral flour or feed use, remilling the isolated coarser grind and further sieving it to obtain an instant corn flour for chips and third generation (3G) foods, and admixing only a fine flour with lime to produce masa flour for tortillas and the like.

BRIEF DESCRIPTION OF THE DRAWINGS

The invention will be more fully understood from the description, which follows, and from the appended drawing in which the sole drawing FIGURE depicts an embodiment of this invention in a block-type flowchart illustrating the continuous and industrial process using a low-temperature and near neutral-pH precooking with an endoxylanase and endoamylase solution as a processing aid.

DETAILED DESCRIPTION OF THE PREFERRED EMBODIMENTS

Figure 1:
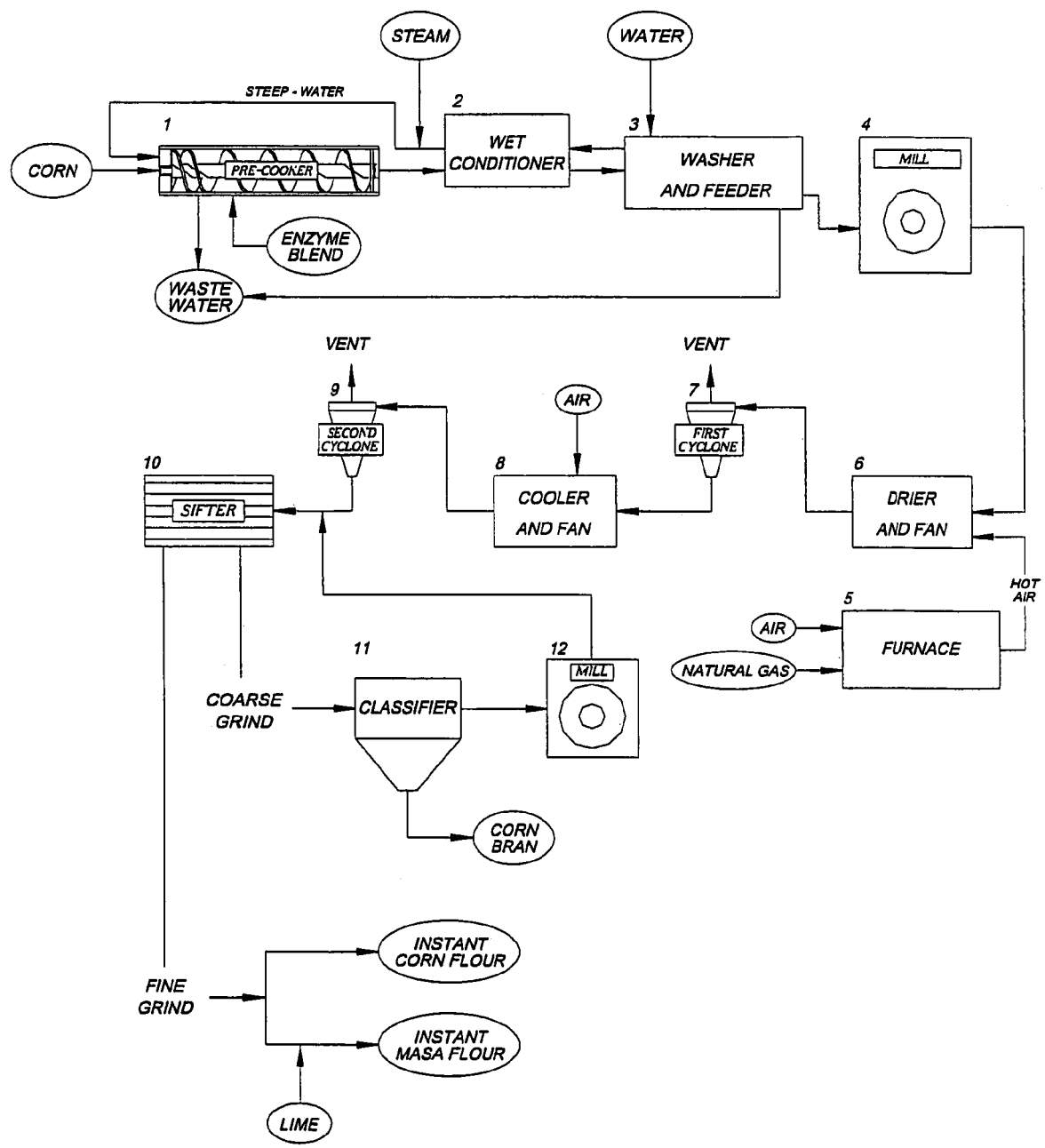

Referring first to FIG. 1, there is depicted, in flowchart form, an embodiment of the present invention. It includes a pre-cooker 1; a wet-conditioner 2; a washer 3 with a feeder; a primary mill 4; a furnace 5; a dryer 6 with a fan; a first cyclone separator 7; a cooler 8 with an associated fan; a second cyclone separator 9; a sifter 10; a classifier system 11; and a secondary mill 12.

The pre-cooker 1, whose design is known per se, is fed with cleaned corn and a hot steep-water (85° C. to 90° C.) recycled from the wet conditioner 2 to form an aqueous suspension (corn to water ratio of about 1:1 to 1:1.5). The corn kernel is parboiled in order to loosen their bran cell walls and partially hydrated from a range of 9%–12% to a range of about 24%–27% for a period of about 20 to about 60 minutes. There is a rapid initial absorption followed by a slower subsequent hydration directly proportional to its kernel immersion time.

Next, a microbial xylanase and amylase solution is continuously added as a food processing aid into the pre-cooker at a low-temperature range of about 50° C. to 70° C. for another period of 75 to 120 minutes. This allows the enzymatically precooked kernel to be produced at moisture contents of between 31% and 34%, while the pH is maintained at a near neutral-pH of about 6.0 to about 8.0 with the addition of a 10% endoxylanase and endoamylase solution to supply from 0.025% to about 0.250% by weight processing aid (based on cleaned corn). By controlling the steam heating along with the kernel residence time, it is possible to precook the corn at a temperature of about 50° C. to 90° C. for a total period of 95 to about 180 minutes in order to permeate their bran layers.

Wastewater loss in the precooker is replaced with recycled steam-heated water from the downstream wet conditioner 2, which is regulated to maintain the soluble-solids content of the suspension from about 0.8% to about 1.6%. The industrial pre-cooker performs a partial hydrolysis of corn bran and starchy cell-walls that promotes a fast water diffusion through the pericarp and tip cap layers, and later on a slow penetration via the endosperm and germ cell-walls increasing starch granule swelling. This continuous enzymatic precooking (i.e., below the gelatinization temperature or <70° C.) further controls both dietary fiber and starch hydrolysis (from about 0.6% to about 1.2% soluble solids), thus permitting a 40% reduction in steep-water solids loss as compared to the traditional alkali cooking (e.g., >2% dissolved solids; U.S. Pat. Nos. 6,516,710 and 4,513,018). The partially precooked corn suspension is then passed to a wet-conditioner 2, whose design is known per se, where it is equilibrated with recycled warm-water from the washer 3, to achieve a uniform residual moisture content of about 34% to about 38% for about 15 to about 60 minutes transit time through the unit.

The conditioned corn is thereafter passed to a washer 3, where it is sprayed with ambient-water in order to stabilize its moisture level from about 38% to about 40% and wash off soluble solids with denatured endoxylanase and endoamylase as wastewater.

Thereafter, the conditioned and washed corn is fed through a feeder, whose design is known per se, to a primary mill 4 such that the premilled corn and hot air coming from a furnace 5, is mixed and partially cooked by an industrial dryer 6 whose design is known per se. The premilled kernel is thereby flash dried at a high-temperature from 190° C. to about 230° C. for a short time of 5 sec to about 30 sec. Its starchy endosperm is partially gelatinized or precooked to yield a moisture content of 16% to about 18% depending on the granulation being produced for snacks and tortillas.

Moisture laden-hot air (110° C. to 125° C., and 11% to 13% moisture) is extracted with a first cyclone separator 7 so that further moisture extraction may take place by impelling the drier material through a cooler 8 with an associated fan, thus further decreasing the moisture content from 16–18% to about 9–12% (similar to incoming corn).

After further extraction of moisture laden-warm air (95° C. to 100° C.) with a second cyclone separator 9, the precooked dry particle is directed to a sifter 10 where the fine fraction is separated (under 16–20 to 45–60 mesh) as instant corn flour and the coarser fraction is further separated.

The latter coarse fraction is further separated in the classifier system 11 wherein two fractions are obtained, a light-bran fraction which is isolated as feed or for integral flour with a moisture content between 9% to 12% (representing from about 3% to about 7% of the total weight of incoming corn), and a heavy coarser fraction that is remilled in a secondary mill 12. The milled product from secondary mill 12 is recycled to the sifter 10 for further sieving and producing a homogeneous corn flour for chip and third-generation snacks (3G products). If desired, the instant corn flour can be admixed with food-grade lime (from 0.05% to about 0.25% based on flour) to produce a masa flour for tortilla and the like.

For use in snack manufacture, the instant corn flour is preferably rehydrated by mixing with warm water from a 1:0.8 to about 1:1.0 weight ratio to form a corn dough (from 45 to 50% final moisture) for chips and third-generation foods (from 15% to 30% total oil).

For use in tortilla manufacture, the masa flour made from the present method can be rehydrated with water from a 1:1.1 to about 1:1.3 weight ratio for a masa dough (from 50% to 60% final moisture) used in tortilla and the like (from about 45% to 50% moisture).

In this method, the novel enzymatic precooking results in a 35% to 45% reduction in wastewater corn solid, with correspondingly lower sewage and energy costs, as compared to the industrial methods (1%–1.6% COD). Furthermore, the enzymatic precooking of the invention allows a 50% reduction in lime use if an instant masa flour were produced to improve new flavors in corn-based foods such as savory chips or third-generation snack products. The low-temperature precooking (<70° C.) at near neutral-pH (6–8) using an endoxylanase and endoamylase solution (0.025%–0.250%) not only aids in depolymerization of the cell-wall heteroxylans but also enhances its bran removal. Both endoenzymes hydrolyze the aleurone and starchy endosperm cell-walls facilitating a simultaneous water diffusion and a reduced gelatinization without using either a <0.25% lime (U.S. Pat. Nos. 6,516,710, 6,428,828, 6,344,228 and 6,387,437) or a <0.25% sulfites addition (U.S. Pat. No. 6,322,836 ).

There is furthermore a potential in corn flour yield from 93% to about 97% of the total weight of enzymatically-precooked corn as compared to the commercial alkali-cooking process, which yields 88%. By pregelatinizing the starchy cell-wall material there is a higher degree of bran removal of the outer layers (hull) from the inner or adhering aleurone endosperm layers. Whereas the instant corn flour produced by the novel method may thus comprise a 95% average yield of flour per kilogram of corn, the debranned and degermed flour produced by a typical dry-milling process obtains only a 65%–75% yield for corn meal (coarse grind), or even a 80%–85% yield for an integral arepa flour (U.S. Pat. No. 6,326,045).

Still further, the low-temperature and enzymatically precooked corn flour produced by the present method has a higher nutritional value as compared to the conventional dry-milling, with more dietary fiber and protein left in the flour (INCAP, 1961).

From the foregoing, it will be apparent that it is possible to manufacture a precooked and partially debranned corn flour for snacks and tortillas with an enzymatic precooking which is efficient because of partial hydrolysis of bran cell-walls and solubilization of the endosperm periphery with starch pregelatinization in the precooked corn kernel, wherein some of the nutrient losses that would have been present but for the features of this invention are prevented. The following table gives a typical nutrient average composition of precooked flours for corn food and traditional tortilla food (INCAP, 1961 and Sustain, 1997):

It is to be understood that the embodiments of this invention herein illustrated and described in detail, are by way of illustration and not of limitation. Other changes and modifications are possible and will present themselves to those skilled in the prior art and by the spirit of the appended claims.

We claim:

1. A biochemical process for the continuous production of precooked and partially debranned corn flour, comprising the steps of:

precooking cleaned corn kernel with steep-water heated from a downstream wet conditioner to form a suspension of corn and water, having a corn to water ratio between 1:1 and 1:1.5, precooking the corn kernel at a near neutral-pH with a solution comprising at least one enzyme selected from the group consisting of an endoxylanase and an endoamylase, to effect a partial hydrolysis of bran heteroxylans and starchy cell-walls during precooking, wet conditioning said precooked kernel to a predetermined moisture range with warm water from a downstream washer, washing said conditioned precooked kernel to remove soluble solids and denatured said at least one enzyme, stabilizing a moisture content of said washed precooked corn kernel with water, milling said washed precooked corn kernel and drying said milled corn kernel for further pregelatinization, cooling and further drying said milled and dried corn kernel, sifting said dried milled corn kernel to obtain a fine fraction, under 16 to 60 mesh to produce a corn flour with fine particle size, and a coarse fraction, and aspirating said sifted coarse fraction to remove a corn bran.

2. The method of claim 1 wherein said enzymatic precooking uses an endoxylanase and endoamylase mixture in an amount from 0.025% to about 0.25% by weight of the corn kernel.

3. The method according to claim 1 wherein said corn bran is a light fraction, representing a minimum yield from 2% to about 3% of the total weight of corn kernel.

4. The method of claim 1, wherein wastewater produced by the enzymatic precooking and washing steps comprises a corn solids reduction in a range of 35% to about 45%.

5. The method in accordance with claim 1, further comprising rehydrating said corn flour by mixing with warm water from a 1:0.8 to about 1:1.0 weight ratio to form a corn dough.

6. The method in accordance with claim 1, further comprising a step of admixing said corn flour with 0.05% to 0.25% by weight lime to produce a masa flour.

7. The method according to claim 6, further comprising a step of rehydrating said masa flour with water from a 1:1.0 to about 1:1.3 weight ratio to form a masa dough.

8. The method of claim 5, wherein the corn dough has a final moisture content between 45% and 50%.

9. The method of claim 7, wherein the masa dough has a moisture in a range of 50% and 55%.

10. The method of claim 1, wherein the at least one enzyme is selected from microbially derived enzymes that are recognized as at least one of GRAS substances and used as processing aids.

11. The method of claim 1, wherein the precooking step is performed up to the denaturing temperature of said endoxylanase and endoamylase.

12. The method of claim 1, wherein in the milling and drying step, the drying is performed with a high temperature-short time drier.

13. The method of claim 1, further comprising remilling the aspirated coarse fraction.

14. The method of claim 13, wherein the remilled coarser fraction is recycled to the sifting step.

* * * * *